United States Patent [19]
York

[11] Patent Number: 5,782,837
[45] Date of Patent: Jul. 21, 1998

[54] ESOPHAGUS CLEARING DEVICE

[76] Inventor: Richard York, 4792 Old Scottsville Rd., Alvanton, Ky. 42122

[21] Appl. No.: 842,040

[22] Filed: Apr. 23, 1997

[51] Int. Cl.⁶ ............................................. A61B 17/50
[52] U.S. Cl. ........................... 606/106; 604/73; 604/181
[58] Field of Search .......................... 606/106; 604/35, 604/36, 37, 38, 181, 79, 275, 73, 76, 77

[56] References Cited

U.S. PATENT DOCUMENTS

| | | |
|---|---|---|
| 1,735,287 | 11/1929 | Lehmann . |
| 2,292,474 | 8/1942 | Paxton . |
| 3,433,214 | 3/1969 | Silverman . |
| 3,502,069 | 3/1970 | Silverman . |
| 3,946,736 | 3/1976 | Neward . |
| 4,400,168 | 8/1983 | Buechel et al. . |
| 4,662,367 | 5/1987 | Gore, Jr. . |

*Primary Examiner*—Michael Buiz
*Assistant Examiner*—David O. Reip
*Attorney, Agent, or Firm*—Middleton & Reutlinger; Charles G. Lamb

[57] ABSTRACT

A throat and esophagus clearing device includes an elongated object receiving chamber with a trigger housing attached thereto. The trigger housing includes a trigger operably responsive to a compression spring and in operable communication with a diaphragm or piston wherein the operation of the diaphragm or piston creates a negative pressure in the elongated object receiving chamber thereby producing a pressure differential, when in use, across an object lodged in a victim's air passageway.

11 Claims, 9 Drawing Sheets

ESOPHAGUS CLEARING DEVICE

BACKGROUND OF THE INVENTION

The present invention relates to a device for clearing lodged objects in the esophagus and more particularly to a hand held device for clearing objects lodged in the esophagus.

When objects, particularly food, become lodged in the throat or esophagus, this morsel of food prevents the passage of air to and from the lungs. If such blockage is complete the victim has approximately two to three minutes before they become unconscious and within approximately five minutes brain damage occurs and shortly thereafter death will result. In treating victims with a large morsel of food lodged in the throat or esophagus there are several first aid measures presently utilized to try and dislodge the trapped morsel of food. One such method is to force the victim to cough by bending the person over and giving them a hard slap between the shoulder blades; a second method includes cutting a hole through the victim's neck into the windpipe to create an emergency air passageway; and, a third method includes squeezing roughly the upper abdomen of the victim in anticipation of expelling the object blocking the air passage. In many cases, the hard slap between the shoulder blade does little to dislodge the object and in many cases the person attempting to provide an abrupt squeeze of the upper abdomen of the victim does not produce the intended results. Moreover, one trained to cut a hole through the neck into the windpipe of the victim is not generally available within the extremely short time before permanent damage or death occurs.

In the prior art there are at least two teachings of devices for the removal of trapped objects in the throat or esophagus. U.S. Pat. No. 3,946,736 teaches a respirator assist device which includes a tubular member insertable into the mouth of a victim in flow communication with a hand operated vacuum pump. And, U.S. Pat. No. 4,662,367 teaches a trachea suction tube including a tubular member having one end insertable into a victim and an opposed end for insertion into the mouth of a life saving person with a filter disposed within the tube so that upon the application of suction by the life saving person, the object and the fluids therefrom are removed by the filter in the tubular member.

SUMMARY OF THE INVENTION

An object of the present invention is to provide a device for removing objects from the throat or esophagus of a victim.

Another object of the present invention is to provide a throat and esophagus clearing device which is easily manipulated by an unskilled person.

A further object of the present invention is to provide a clearing device for the throat and esophagus of a victim which applies a suction to the mouth and throat of the victim in such a manner that a pressure differential created within the throat and esophagus causes the lodged object to be dislodged and sucked through the clearing device.

It is an even further object of the present invention to provide a throat and esophagus clearing device which is simply constructed and relatively inexpensive.

More particularly, the present invention provides a throat and esophagus clearing device comprising: an elongated object receiving chamber with a trigger housing attached to the receiving chamber, the trigger housing having a trigger means disposed within the housing in operable communication with a moveable wall, such as, a diaphragm or piston disposed within the elongated object receiving chamber wherein the moveable wall creates a negative pressure when activated by the trigger means in turn producing a pressure differential across an object lodged in a user's food passageway.

Additional objects and advantages of the invention will become apparent to those skilled in the art from the following written description and the figures relating thereto.

BRIEF DESCRIPTION OF THE DRAWINGS

The preferred embodiments of the invention will be described herein with reference to the numerals set forth in the figures wherein.

DESCRIPTION OF THE PREFERRED EMBODIMENT

Figure 1:
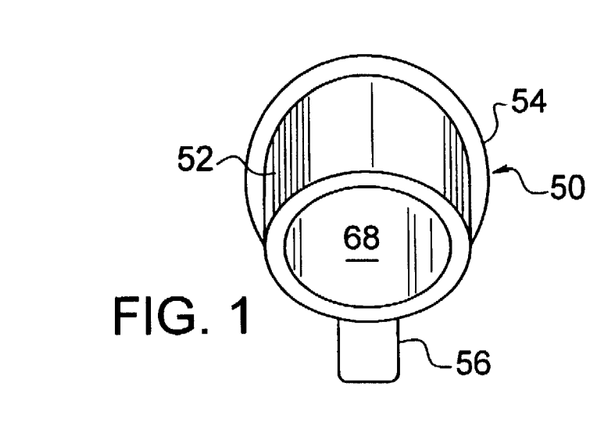
FIG. 1 is a front view of a throat and esophagus clearing device of the present invention.
Figure 2:
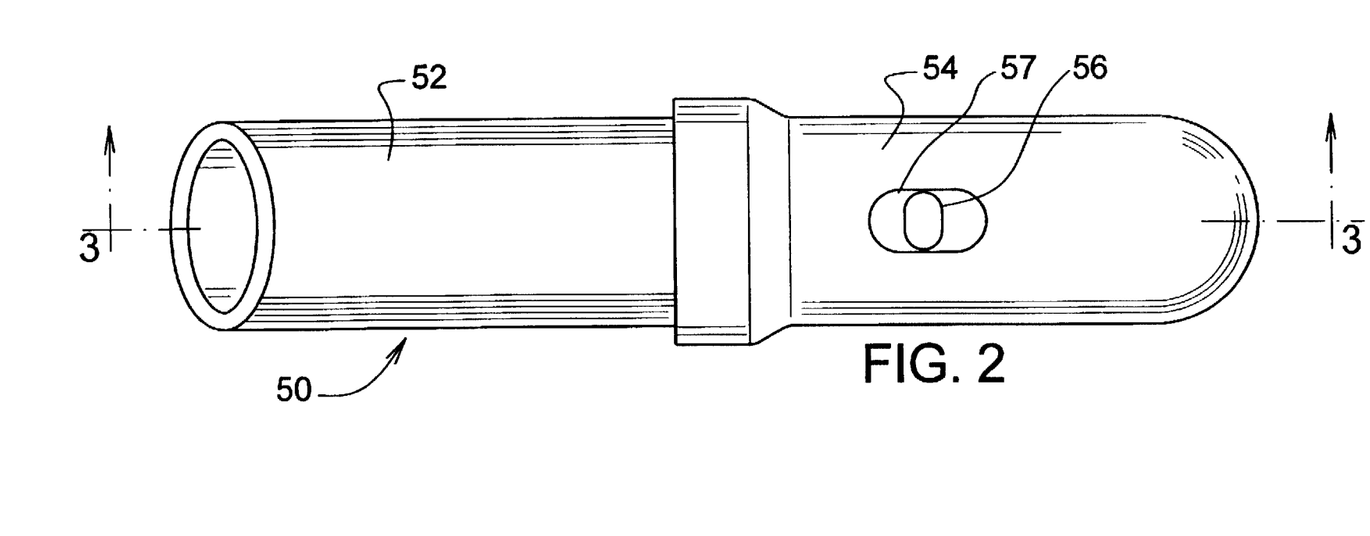
FIG. 2 is a bottom view of one throat and esophagus clearing device of FIG. 1.

Referring to FIGS. 1 and 2, a throat and esophagus clearing device 50 is shown. The throat and esophagus clearing device 50 includes an elongated object receiving chamber 52 attached to a trigger housing 54. Preferably, the central axis of chamber 52 and housing 54 are axially aligned. The receiving chamber 52 is provided with an opening 68 therein to receive objects dislodged from the air passageway of a victim. The trigger housing includes a movable trigger 56 received within a slot 57 for pivotal movement from a cocked to an uncocked position.

Figure 2A:
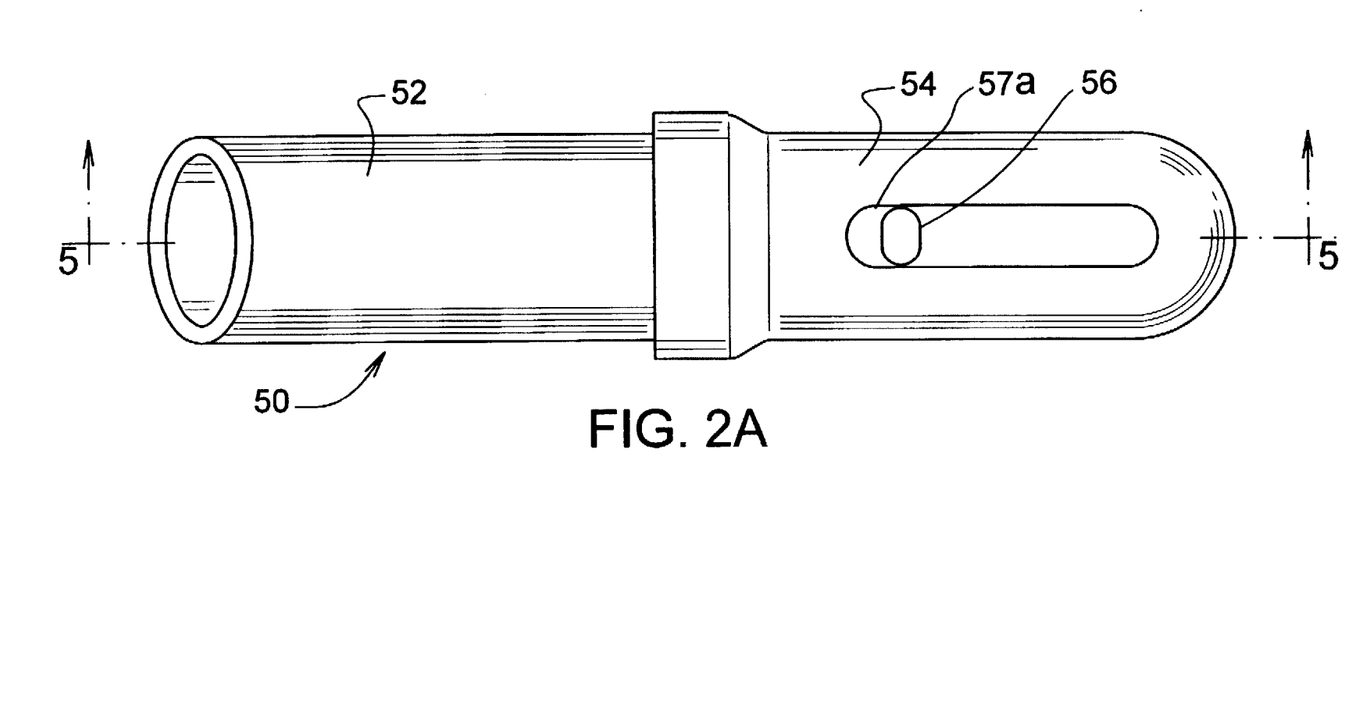
FIG. 2A is a bottom view of a modification of the embodiment of a throat and esophagus clearing device of FIG. 1.

In FIG. 2A, a modification of the embodiment of the clearing device of FIG. 1 is shown with an elongated slot 57a for trigger travel along a horizontal path.

Figure 3:
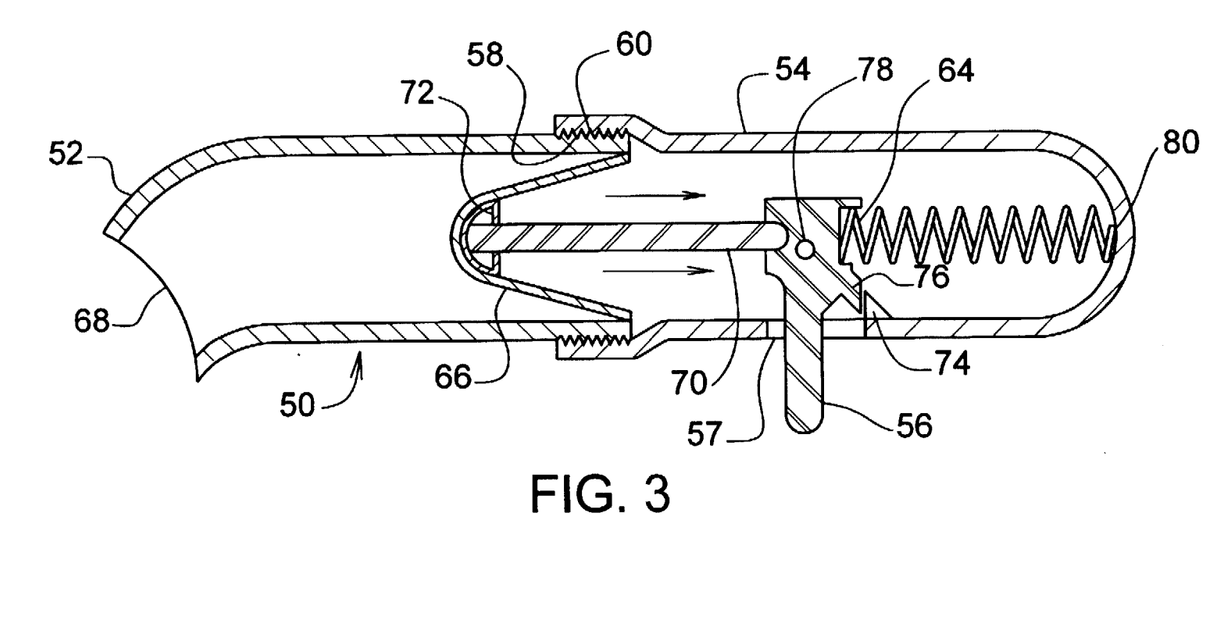
FIG. 3 is a sectional view of FIG. 2 taken along line 3—3.
Figure 3A:
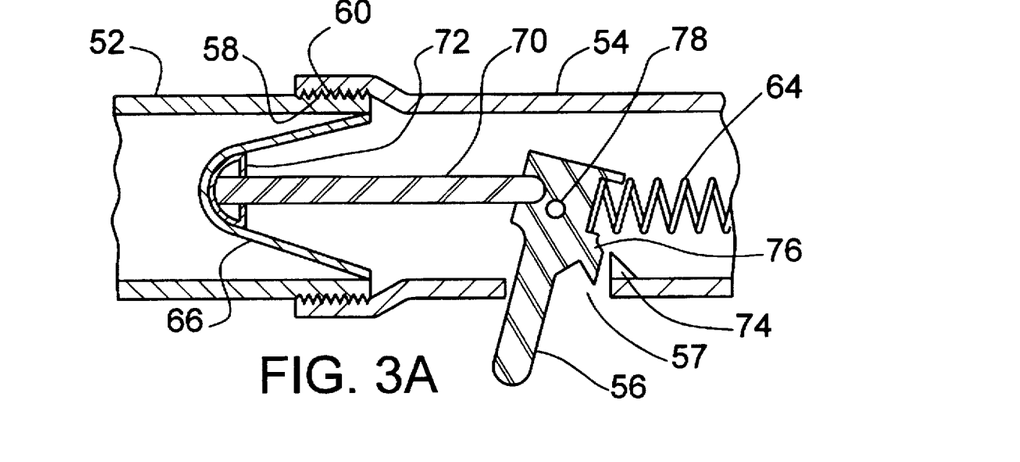
FIG. 3A is the sectional view of FIG. 3 showing the throat and esophagus clearing device in an uncocked position.
Figure 3B:
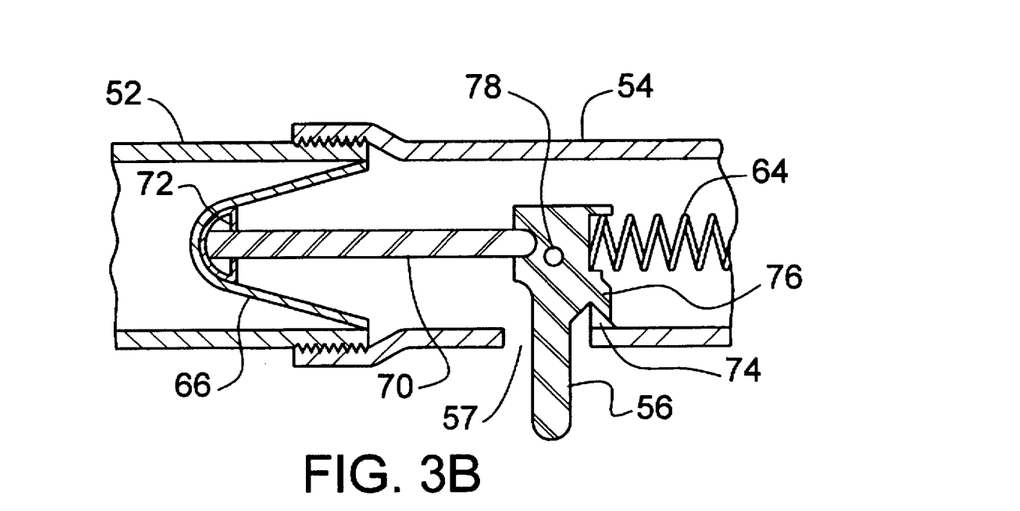
FIG. 3B is the sectional view of FIG. 3 showing the throat and esophagus clearing device in a cocked position.

Now referring to the sectional views FIGS. 3, 3A, and 3B, the throat and esophagus clearing device shows the receiving chamber 52 threadably received within the trigger housing 54 as shown by male threads 58 on the receiving chamber 52 and the female threads 60 of the trigger housing 54. The trigger housing 54 includes a cocking trigger 56 pivotally attached to the housing 54 by a transversely extending pin 78. A longitudinally extending connecting member 70 is connected to the trigger 56 on one end and a hemispherically shaped diaphragm moving member 72 on an opposed end. The hemispherically-shaped member 72 is positioned for engagement with a diaphragm 66 which is usually detachably connected along an inner peripheral surface of the receiving chamber 52 adjacent to the attachment of the chamber 52 and the housing 54.

The trigger 56 is attached to and operably responsive to a tension on spring 64 which is fixedly attached at its opposite end to the trigger at the location designated by the numeral 80 of the trigger housing 54. The trigger 56 is provided with a trigger release 76 which is engageable with a cocking catch 74 which is disposed at a preselected position along the inner surface of the trigger housing 54.

As best shown in FIG. 3A, when the trigger release finger 76 is disengaged from the cocking catch 74, the tension on spring 64 pulls the trigger 56 to its rearward most position. In FIG. 3B, when the trigger release 76 is in latching position with the cocking catch 74, the tension on spring 64 is stretched and the cocked trigger 56 is in its forwardmost position. Simultaneously the diaphragm 66 is forced inwardly into the reservoir 52 by the inward movement of the longitudinal connecting member 70 inward movement and the engagement of the hemispherically shaped member 72 with the diaphragm 66.

Figure 3C:
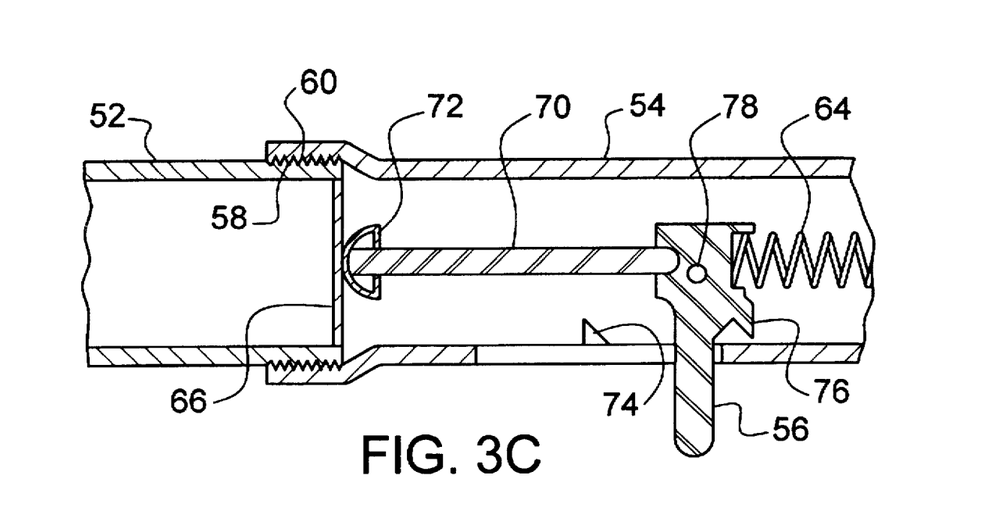
FIG. 3C is a sectional view of the modification of FIG. 2A taken along line 5—5 showing the embodiment in an uncocked position.
Figure 3D:
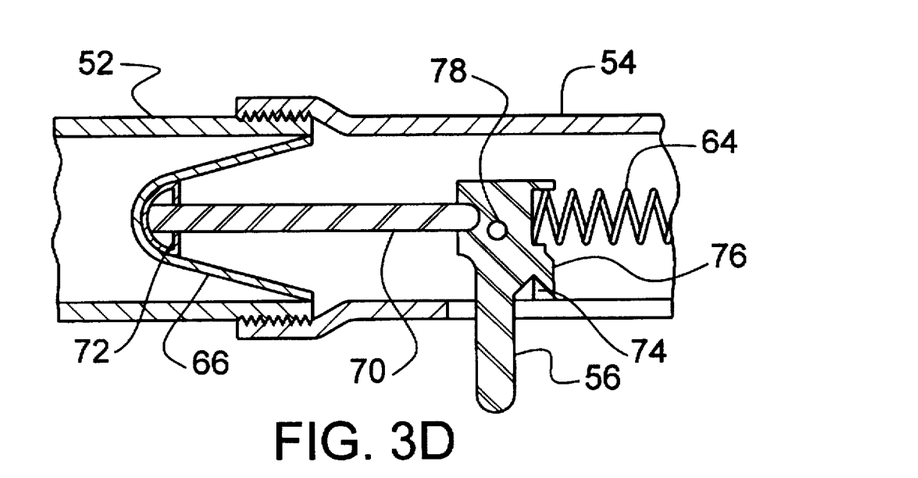
FIG. 3D is the sectional view of FIG. 3C showing the embodiment in a cocked position.

FIGS. 3C and 3D show a modification of the embodiment of FIGS. 3A, 3B in a trigger uncocked and cocked position, respectively, when the trigger 56 is attached to a diaphragm 72 through an elongated connecting member 70 and the trigger 56 is moveable within a slot, such as 57a, as shown in FIG. 2A.

Figure 4:
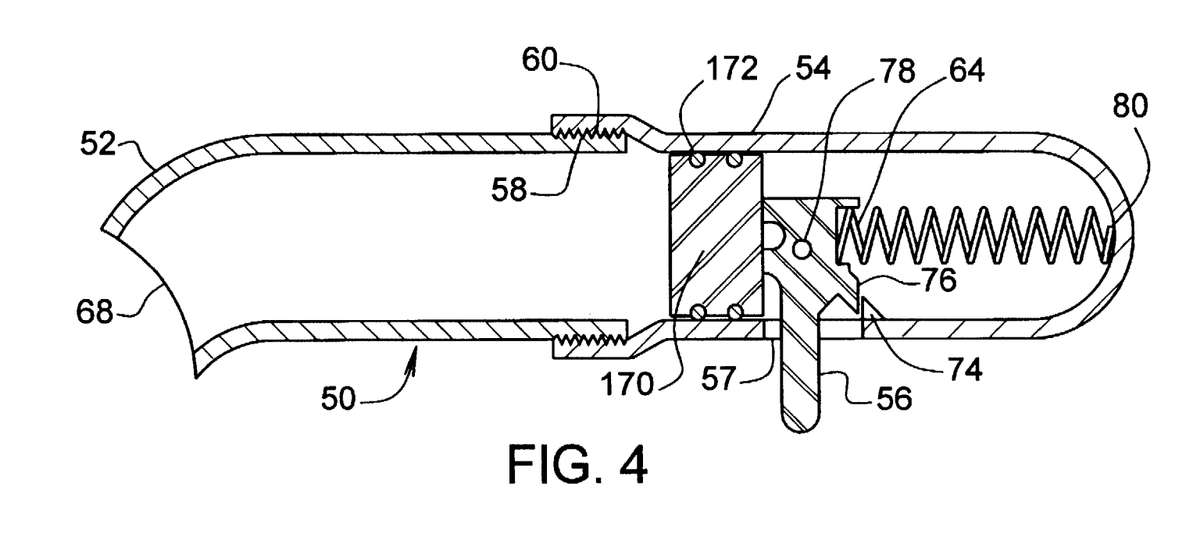
FIG. 4 is a sectional view of another modification of FIG. 2 taken along line 3—3.
Figure 4A:
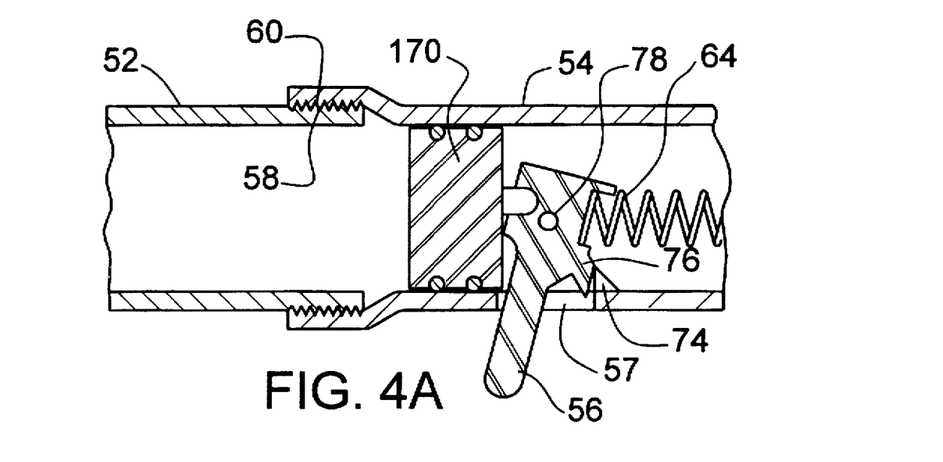
FIG. 4A is the sectional view of FIG. 4 showing the clearing device in an uncocked position.
Figure 4B:
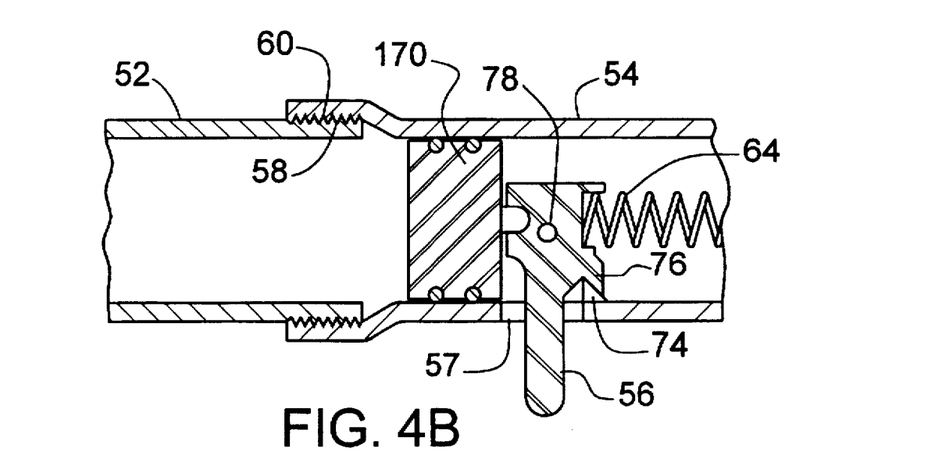
FIG. 4B is the sectional view of FIG. 4 showing the clearing device in a cocked position.

Referring to FIGS. 4, 4A, 4B, the throat and esophagus clearing device is shown with the longitudinally extending connecting member 70 and diaphragm moving member 72 being replaced by a piston 170 which moves from a cocked position as shown in FIG. 4B to an uncocked position as shown in FIG. 4A. The piston 170 is generally attached to the trigger 56. Also, a plurality of "O" rings 172 are provided along the outer surface of the piston 172 for sealing between the piston 172 and the inner surface of trigger housing 54 as well as aiding the movement of the piston 172 from a cocked to an uncocked position. It is also realized that other sealing means may be used, such as, for example, V-ring seals.

Figure 5:
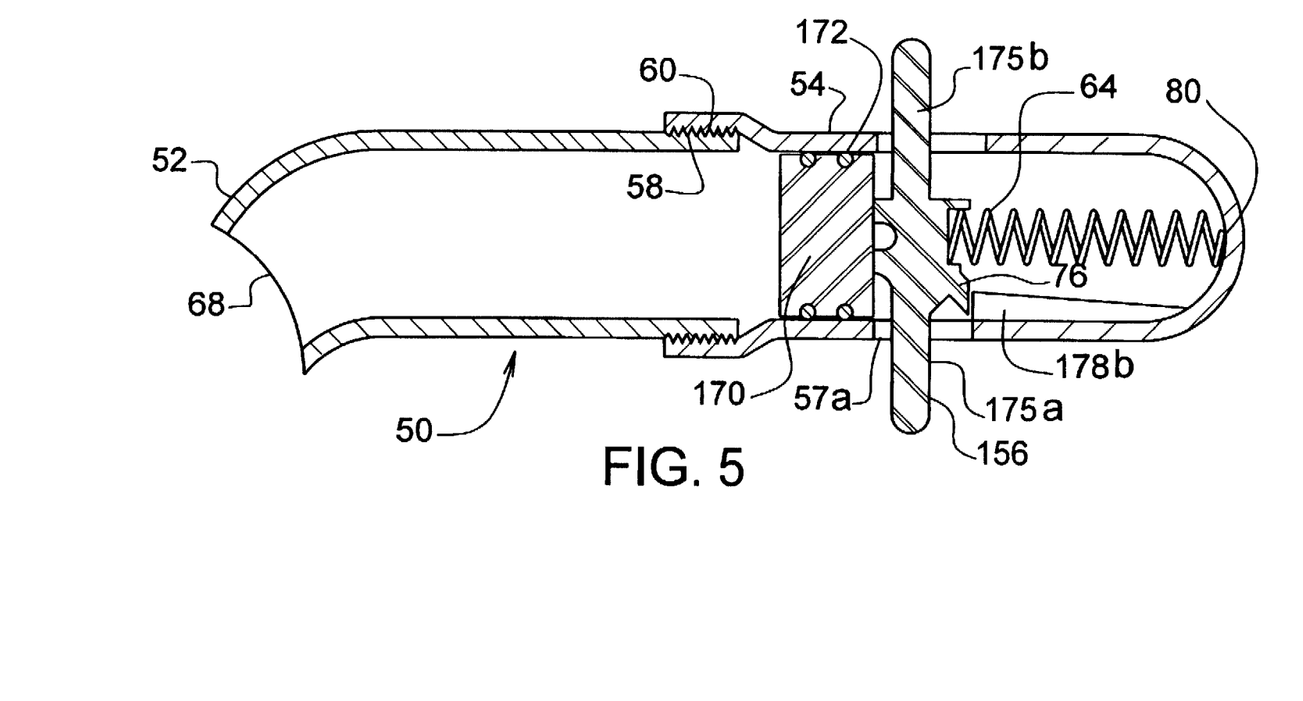
FIG. 5 is a sectional view of another embodiment of FIG. 2A taken along line 5—5.
Figure 6:
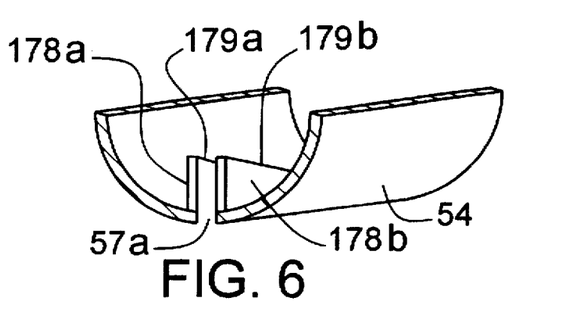
FIG. 6 is an enlarged perspective view of one section of the clearing device of FIG. 5; and, FIG. 7 is a longitudinal sectional view of a throat and esophagus clearing device of the present invention positioned within a person's mouth adjacent portions of the mouth and throat indicated in section and showing a typical location of a lodged object in an air passageway of a victim.

Referring to FIG. 5, the throat and esophagus clearing device is provided with a double trigger finger 175a, 175b for cocking trigger 156. Also, trigger 156 is not moveable by pivoting trigger 156 but is moveable in a slot 57a in the housing 54. As best shown in FIG. 6, slot 57a is in cooperating relation with wedge-shaped members 178a and 178b on opposite sides of slot 57a to receive trigger release 76 along the declining upper surfaces 179a and 179b of members 178a, 178b as the trigger 156 moves from a cocked to an uncocked position. It is realized in this embodiment that the spacing between members 178a and 178b is less than the thickness of the trigger release 76.

Figure 7:
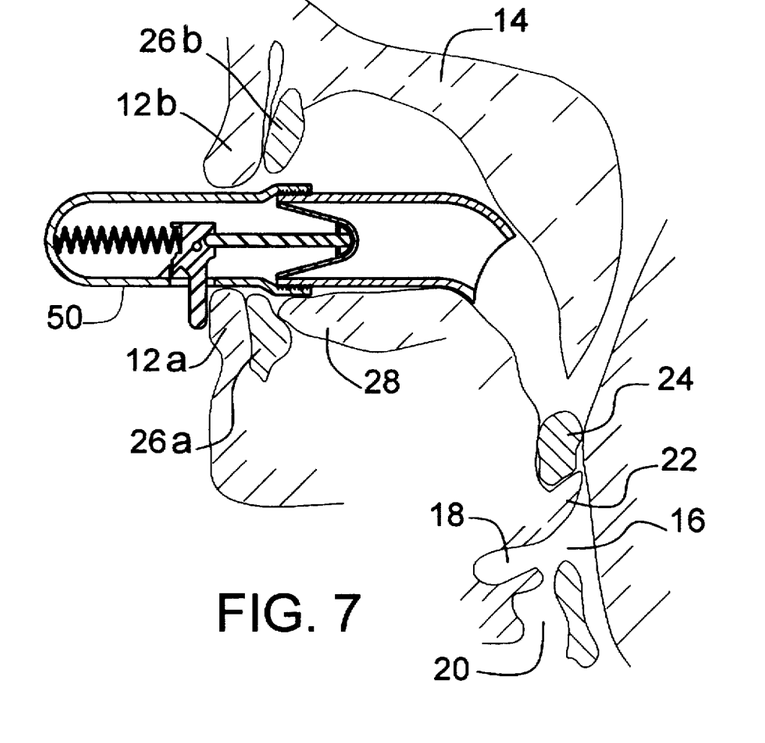

Referring now to FIG. 7, FIG. 7 shows a partial sectional view of the head of a victim with the esophagus clearing device 50 inserted into the mouth of the victim. As shown, the clearing device 50 is inserted between the lips 12a, 12b, and the teeth 26a, 26b and over the tongue 28. The clearing device 50 is of sufficient length to extend beneath the pallet 14 and is in flow communication with the air passageway which includes the larynx 18, the trachea 20, and the esophagus 16. As shown, a particle of food 24 is lodged in the air passageway and caught by the esophagus 22. In operation, the trigger 56 of the clearing device 50 is cocked and upon insertion into the mouth of the victim, the trigger 56 is then released wherein the diaphragm or piston returns to its uncocked position thereby creating a vacuum within the receiving chamber 52 which in turn creates a differential pressure in the air passageway thereby dislodging the lodged food particle 24. Moreover, since the receiving chamber 54 and the trigger housing 56 are threadably connected, removing chamber 54 from attachment to housing 56 enables easy access for cleaning and removal of objects from the receiving chamber 56.

Even though the size of the clearing device 50 has not been set forth in terms of length or diameter, it is realized that various lengths and diameters will be necessary to accommodate adult men, adult women and various sizes to accommodate children of various ages. Moreover, the clearing device may be made of any known materials of construction, but a single piece of molded plastic for each of the receiving chamber 52 and the trigger housing 54 which are capable of sterilization and sufficiently low in cost are preferred.

Even though only one embodiment with selected modifications has been shown and described in the present application, it is realized that other modifications may be made to the preferred embodiment without departing from the scope and spirit of the present invention as set forth in the claims appended hereto.

What is claimed is:

1. A throat and esophagus clearing device comprising:
   an elongated object receiving chamber;
   a trigger housing threadably connected at a junction to said elongated object receiving chambers, said trigger housing being provided with a central axis in axial alignment with a central axis in said elongated object receiving chamber; and,
   means within said trigger housing to create a negative pressure in said elongated object receiving chamber.

2. The clearing device of claim 1, said means to create a negative pressure in said elongated object receiving chamber including a trigger disposed within said trigger housing in operable communication with a diaphragm, movement of said diaphragm creating a negative pressure in said elongated object receiving chamber.

3. The clearing device of claim 1, wherein said trigger housing includes a trigger operably responsive to tension means therein.

4. The clearing device of claim 1, said trigger housing including a trigger therein having a trigger release in mating relation with a catch attached to an inner wall of said trigger housing.

5. The clearing device of claim 1, said trigger housing including therein a longitudinally extending connecting rod attached to a trigger on one end, said rod being engageable with a diaphragm on an opposed end from said one end.

6. The clearing device of claim 1, including a diaphragm detachably connected to an inner peripheral surface of said receiving chamber whereby movement of said diaphragm creates said negative pressure in said object receiving chamber.

7. The clearing device of claim 6, said diaphragm being positioned adjacent to the junction of said object receiving chamber and said trigger housing.

8. The clearing device of claim 1, including a trigger disposed within said trigger housing in operable communication with a piston, movement of said piston creating said negative pressure in said object receiving chamber.

9. The clearing device of claim 1 including a slot in said trigger housing and a trigger moveable within said slot from a cocked position to an uncocked position.

10. The clearing device of claim 9 including a wedge-shaped member extending along said slot, said wedge-shaped member having an upper surface reclining from said cocked position to said uncocked position.

11. The clearing device of claim 1, including a trigger within said trigger housing, said trigger having two opposed fingers extending through opposite slots in said housing.

* * * * *